United States Patent
Salo et al.

(10) Patent No.: US 7,630,761 B2
(45) Date of Patent: Dec. 8, 2009

(54) METHOD AND APPARATUS FOR MODIFYING TISSUE TO IMPROVE ELECTRICAL STIMULATION EFFICACY

(75) Inventors: Rodney W. Salo, Fridley, MN (US); Joseph M. Pastore, Woodbury, MN (US); Haris J. Sih, Minneapolis, MN (US); Jihong Qu, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 575 days.

(21) Appl. No.: 11/267,654

(22) Filed: Nov. 4, 2005

(65) Prior Publication Data

US 2007/0106202 A1  May 10, 2007

(51) Int. Cl.
*A61N 1/18* (2006.01)
(52) U.S. Cl. ............................. 607/3; 607/120
(58) Field of Classification Search ................ 607/3, 607/21, 120; 604/157; 600/547, 554
See application file for complete search history.

(56) References Cited

U.S. PATENT DOCUMENTS

| | | | |
|---|---|---|---|
| 4,360,031 A | 11/1982 | White | |
| 5,697,951 A * | 12/1997 | Harpstead et al. | 607/3 |
| 6,059,726 A | 5/2000 | Lee et al. | |
| 6,141,594 A | 10/2000 | Flynn et al. | |
| 6,165,164 A | 12/2000 | Hill et al. | |
| 6,254,573 B1 | 7/2001 | Haim et al. | |
| 6,309,370 B1 | 10/2001 | Haim et al. | |
| 6,463,334 B1 | 10/2002 | Flynn et al. | |
| 6,514,952 B1 * | 2/2003 | Stilz et al. | 514/89 |
| 6,540,725 B1 | 4/2003 | Ponzi | |
| 6,575,931 B1 | 6/2003 | Ponzi | |
| 6,623,473 B1 | 9/2003 | Ponzi | |
| 6,623,474 B1 | 9/2003 | Ponzi | |
| 6,628,988 B2 * | 9/2003 | Kramer et al. | 607/9 |
| 6,702,777 B2 | 3/2004 | Haim et al. | |
| 6,855,124 B1 | 2/2005 | Gonzalez et al. | |
| 6,905,476 B2 | 6/2005 | Ponzi | |
| 6,915,169 B2 | 7/2005 | Flynn et al. | |
| 7,245,973 B2 | 7/2005 | Liu et al. | |
| 7,320,675 B2 | 1/2008 | Pastore et al. | |
| 2002/0183720 A1 | 12/2002 | Hill et al. | |
| 2003/0113303 A1 | 6/2003 | Schwartz | |
| 2003/0125615 A1 | 7/2003 | Schwartz | |
| 2003/0129750 A1 | 7/2003 | Schwartz | |
| 2003/0171723 A1 | 9/2003 | Ponzi | |
| 2003/0195470 A1 | 10/2003 | Ponzi | |
| 2003/0204206 A1 * | 10/2003 | Padua et al. | 607/2 |
| 2004/0068312 A1 * | 4/2004 | Sigg et al. | 607/120 |

(Continued)

OTHER PUBLICATIONS

US 6,875,206, 04/2005, Ponzi (withdrawn)

*Primary Examiner*—Carl H Layno
*Assistant Examiner*—Brian T Gedeon
(74) *Attorney, Agent, or Firm*—Schwegman, Lundberg & Woessner, P.A.

(57) ABSTRACT

A biologic agent delivery system provides for delivery of a biologic agent to a stimulation site to which electrical stimulation pulses are to be delivered from an electrical stimulation device. Examples of the electrical stimulation device include cardiac pacemakers and neural stimulators. The biologic agent modifies tissue property to lower the stimulation threshold of the stimulation site. The genetic modification of the tissue property improves efficacy and/or energy efficiency of an electrical stimulation therapy.

38 Claims, 6 Drawing Sheets

U.S. PATENT DOCUMENTS

| | | | |
|---|---|---|---|
| 2004/0158289 A1* | 8/2004 | Girouard et al. | ............... 607/3 |
| 2004/0158290 A1 | 8/2004 | Girouard | |
| 2004/0213770 A1 | 10/2004 | Seward et al. | |
| 2004/0214182 A1 | 10/2004 | Sharma et al. | |
| 2004/0215251 A1 | 10/2004 | Sharma et al. | |
| 2005/0043675 A1 | 2/2005 | Pastore et al. | |
| 2005/0137671 A1 | 6/2005 | Liu et al. | |
| 2005/0192637 A1 | 9/2005 | Girouard et al. | |

* cited by examiner

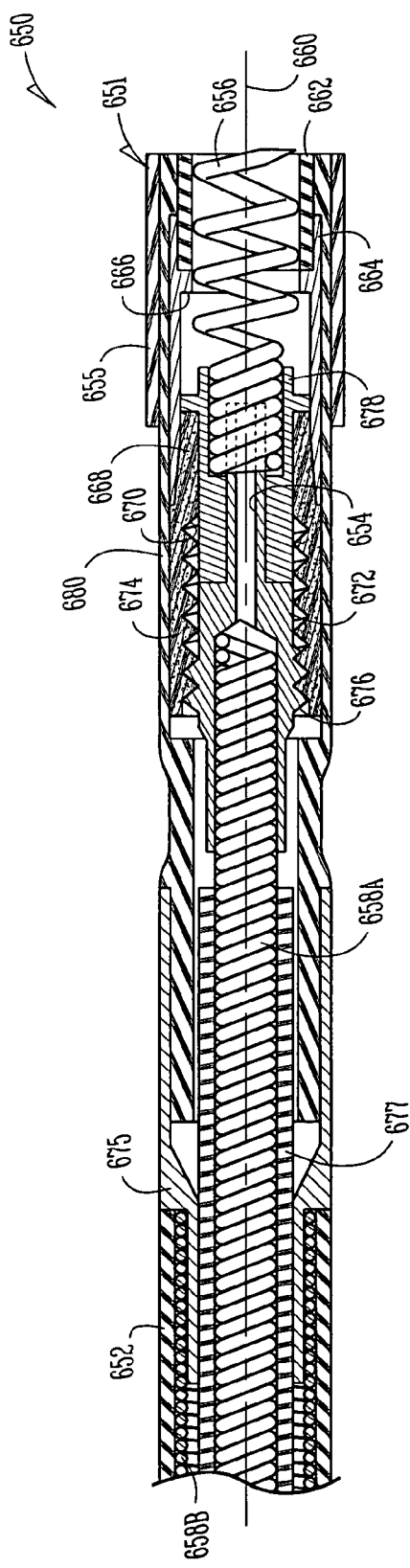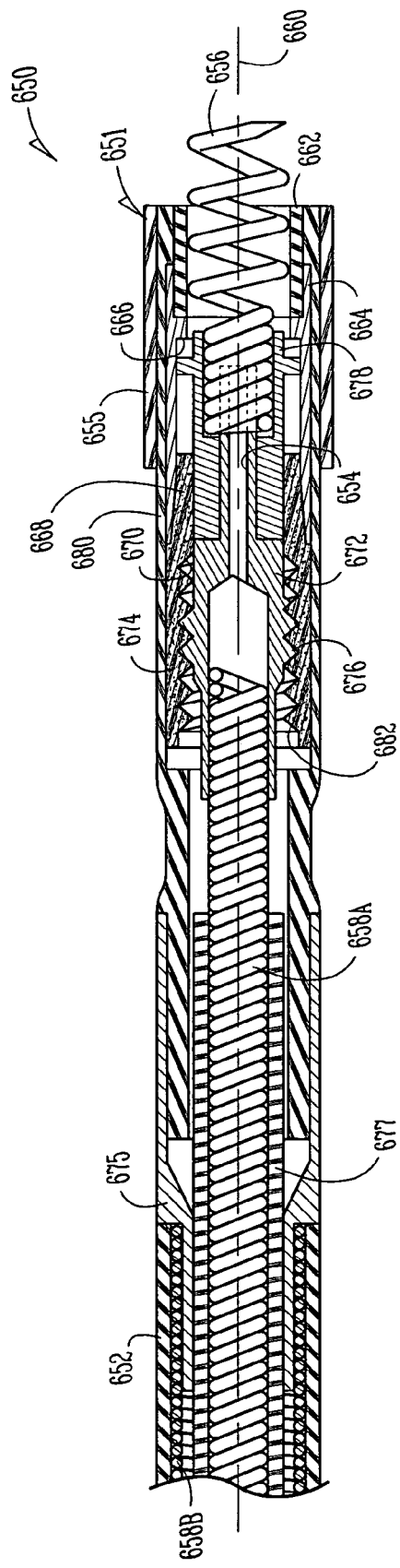

METHOD AND APPARATUS FOR MODIFYING TISSUE TO IMPROVE ELECTRICAL STIMULATION EFFICACY

TECHNICAL FIELD

This document relates generally to implantable medical systems and particularly to method and apparatus for improving efficacy of electrical stimulation therapy by genetically modifying the tissue being stimulated.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium. In a normal heart, the sinoatrial node, the heart's natural pacemaker, generates electrical impulses at a normal cardiac rhythm. The electrical impulses propagate through an electrical conduction system to various regions of the heart to excite the myocardial tissues of these regions. Coordinated delays in the propagations of the electrical impulses in a normal electrical conduction system cause the various portions of the heart to contract in synchrony to result in efficient pumping functions. A blocked or otherwise abnormal electrical conduction and/or deteriorated myocardial tissue cause dysynchronous contraction of the heart, resulting in poor hemodynamic performance, including a diminished blood supply to the heart and the rest of the body.

Implantable pacemakers are used to restore cardiac rhythm and/or synchrony of cardiac contractions by delivering electrical stimulation pulses, known as pacing pulses, to one or more pacing sites in the heart. The minimum level of pacing energy required for a pacing pulse to excite the myocardial tissue in a pacing site is known as the pacing threshold for that pacing site. During implantation of an implantable pacemaker, the pacing threshold is evaluated with respect to each pacing site. The pacing energy delivered by the implantable pacemaker with each pacing pulse to each pacing site is then determined as a value that exceeds the pacing threshold by a safety margin. Under certain circumstances, the pacing energy so determined exceeds the maximum pacing energy level deliverable with each pacing pulse by the implantable pacemaker. This may happen, for example, when the tissue property is altered by a pathological condition or event, such as myocardial infarction. Myocardial tissue in an infarct region generally becomes less electrically excitable, requiring an increased energy level to activate.

Additionally, because the implantable pacemaker is battery-powered, delivering pacing pulses at lower energy levels increases the device longevity. For these and other reasons, there is a need to manage the pacing threshold at each pacing site to improve efficacy and efficiency of a pacing therapy.

SUMMARY

A biologic agent delivery system provides for delivery of a biologic agent to a stimulation site to which electrical stimulation pulses are to be delivered from an electrical stimulation device. Examples of the electrical stimulation device include cardiac pacemakers and neural stimulators. The biologic agent modifies tissue property to lower the stimulation threshold of the stimulation site. The modification of the tissue property improves efficacy and/or energy efficiency of an electrical stimulation therapy.

In one embodiment, a system for delivering electrical stimulation pulses to at least one stimulation site in a body includes a reservoir containing at least one biologic agent and a biologic agent delivery device. The biologic agent modifies tissue property to lower a stimulation threshold. The biologic agent delivery device, which includes the reservoir or is coupled to the reservoir, delivers the biologic agent from the reservoir to the stimulation site.

In one embodiment, a method for delivering electrical stimulation pulses to at least one stimulation site in a body is provided. At least one biologic agent is delivered to the stimulation site. The biologic agent modifies tissue property in the stimulation site to lower a stimulation threshold. The electrical stimulation pulses are then delivered to the stimulation site to cause tissue excitation.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 6A is an illustration of an embodiment of a distal end of a pacing lead including a biologic agent delivery device.

FIG. 6B is another illustration of the embodiment of the distal end of the pacing lead including the biologic agent delivery device.

DETAILED DESCRIPTION

Figure 1:
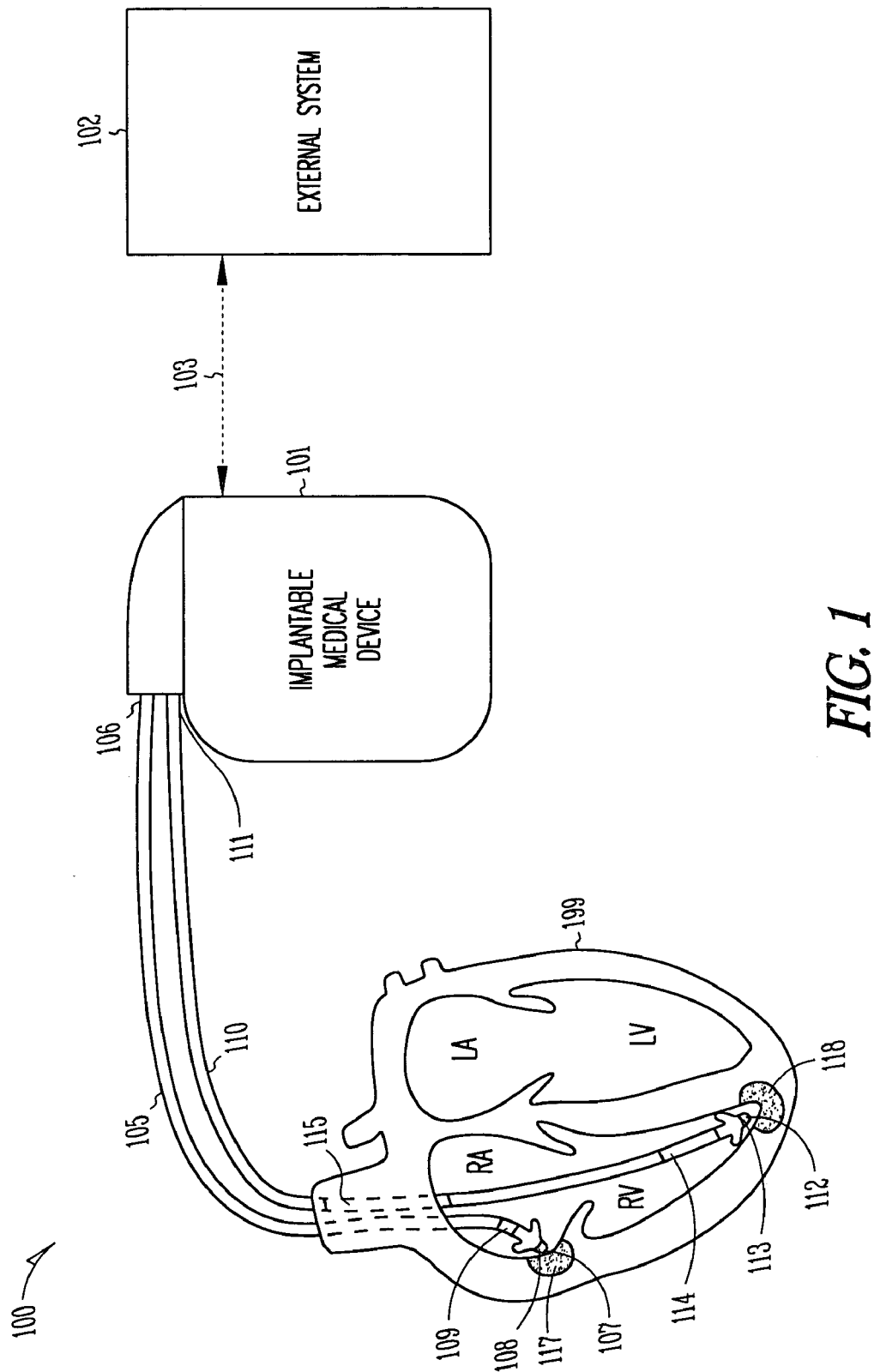
FIG. 1 is an illustration of an embodiment of a cardiac rhythm management (CRM) system delivering pacing pulses to stimulation sites with genetically modified tissue and portions of an environment in which the CRM system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses system and method for genetically modifying tissue at a stimulation site to which electrical stimulation pulses are delivered. The modification of the tissue alters the property of the tissue to result in a lower stimulation threshold, which is the minimum level of energy required for each stimulation pulse to excite the tissue at the stimulation site. While cardiac pacing therapy delivered by an implantable medical device is specifically described below as an example, the present subject matter generally applies to all electrical stimulation therapies delivered by various types of implantable and non-implantable medical devices.

According to the present subject matter, at least one biologic agent is delivered to each selected pacing site to lower the pacing threshold of that pacing site. Examples of the biologic agent include genetically modified cells, recombinant viruses, and isolated nucleic acid, e.g., isolated deoxyribonucleic acid (DNA) or ribonucleic acid (RNA), which encode a desirable (beneficial) gene product. In one embodiment, expression of the gene product in the modified tissue is regulated by an electric field associated with pacing pulses. When turned on by the pacing pulses, the gene expression lowers the pacing threshold of the modified tissue. In one embodiment, the delivery of the biologic agent, either the amount or site, or both, is controlled to limit the modification of tissue at the pacing site that is immediately surrounding a pacing electrode.

The present subject matter improves the efficacy of pacing therapies when the location of a pacing site is important or crucial, or when changing the location of the pacing site is undesirable or considered unsafe. In one example, following a myocardial infarction (MI), pacing pulses are delivered to the infarct region in a remodeling control therapy (RCT). When the pacing threshold at the infarct region requires a pacing energy above the capability of an implantable medical device that delivers the pacing pulses, genetically modifying the tissue of a portion of the infarct region in accordance with the present subject matter makes it possible to deliver the RCT effectively. In another example, to treat a heart having dyssynchronous ventricular contractions, pacing pulses are delivered to one or more ventricular pacing sites in a cardiac resynchronization therapy (CRT). The location of each ventricular pacing site is chosen for optimal restoration of ventricular synchrony. When the pacing threshold at the optimal pacing site requires a pacing energy above the capability of an implantable medical device that delivers the pacing pulses, modifying the tissue at that optimal pacing site in accordance with the present subject matter makes it possible to optimize the effect of the CRT. In a more general example, modifying the tissue at each pacing site in accordance with the present subject matter reduces the overall power consumption of the implantable medical device, thereby extending its longevity.

FIG. 1 is an illustration of an embodiment of a CRM system 100 and portions of an environment in which system 100 is used. System 100 includes an implantable medical device 101 that is electrically coupled to a heart 199 through leads 105 and 110. An external system 102 communicates with implantable medical device 101 via a telemetry link 103.

System 100 delivers electrical stimulation pulses to one or more stimulation sites that have been treated with a biologic agent to modify the tissue property for lowering stimulation thresholds. As illustrated in FIG. 1 as a specific example, the electrical stimulation pulses includes cardiac pacing pulses, and the one or more stimulation sites include one or more pacing sites. In general, the present subject matter is applicable to any electrical stimulation therapy that uses electrical energy to excite portions of body tissue. The tissue at each stimulation site is modified by the biologic agent to lower the stimulation threshold, i.e., the minimum electrical energy required for tissue excitation.

Implantable medical device 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is a pacing lead that includes a proximal end 106 connected to implantable medical device 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to implantable medical device 101 via separate conductors in lead 105 to allow sensing of the atrial electrogram and/or delivery of atrial pacing pulses to a pacing site 117. Lead 110 is a defibrillation lead that includes a proximal end 111 connected to implantable medical device 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to implantable medical device 101 via separate conductors in lead 110. Electrode 113 allows sensing of the ventricular electrogram and/or delivery of ventricular pacing pulses to a pacing site 118. Electrodes 114 and 115 allow delivery of ventricular cardioversion/defibrillation pulses.

Pacing sites 117 and 118 are each biologically treated to lower the pacing threshold. A biologic therapy includes delivering one or more biologic agents to tissue at each of pacing sites 117 and 118 to modify the property of the tissue. In one embodiment, at least one biologic agent is delivered to pacing sites 117 and 118 at the time when implantable medical device 101 is implanted, and the tissue property in these pacing sites is permanently modified. In another embodiment, at least one biologic agent is delivered to pacing sites 117 and 118 repeatedly to maintain a lowered pacing threshold.

In various embodiments, implantable medical device 101 and heart 199 are electrically connected using one or more leads such as leads 105 and 110, other endocardial leads, and epicardial leads. Each lead includes at least one pacing electrode placed in or on a pacing site being an endocardial pacing site, epicardial pacing site, intravascular pacing site, or a pacing site within a cardiac wall. The pacing site is for delivering pacing pulses to stimulate any one or more of the RA, LA, RV, and LV. The biologic therapy is delivered to such a pacing site to modify the tissue surrounding the pacing electrode to lower the pacing threshold for the pacing site.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system allows access to implantable medical device 101 from a remote location, such as for monitoring patient status and adjusting a therapy. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), and programming implantable medical device 101 to deliver one or more therapies, including the biologic therapy for lowering the stimulation threshold.

Figure 2:
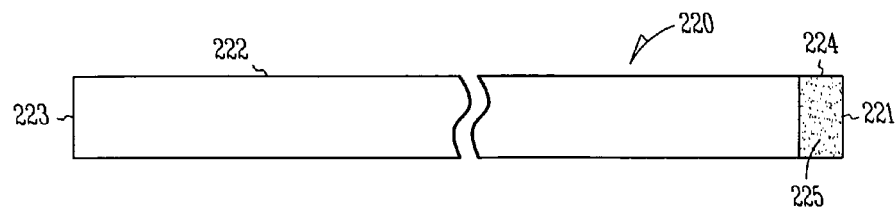
FIG. 2 is an illustration of an embodiment of a biologic agent delivery device.

FIG. 2 is an illustration of an embodiment of a biologic agent delivery device 220. Biologic agent delivery device 220 includes a distal end 221, a proximal end 223, and an elongate body 222 coupled between distal end 221 and proximal end 223. Distal end 221 is configured to reach a stimulation site such as pacing site 117 or 118. Biologic agent delivery device 220 includes an agent eluting device 224 located at distal end 221. Agent eluting device 224 includes a reservoir that contains a biologic agent 225. After being introduced to tissue, biologic agent 225 modifies the property of the tissue to lower its stimulation threshold, i.e., after introduction of the biologic agent in an effective amount, the tissue is more easily excitable with electrical energy. In one embodiment, biologic agent 225 includes one or more of genetically modified cells, such as genetically modified stem cells, recombinant viruses, or nonviral vectors, e.g., a DNA or RNA vector, which include one or more open reading frames that encode a gene product that renders tissue more excitable when exposed to electrical energy. In one embodiment, the open reading frame is operably linked to a transcriptional element (e.g., a promoter) regulatable by an electric field created by the pacing pulses. In one embodiment, genetically modified cells, recombinant virus or isolated nucleic acid encode one or more subunits of a sodium (Na) or L-type calcium (Ca) channel, the expression of which increases excitability of cells. In one embodiment, genetically modified cells, recombinant virus or isolated nucleic acid encode connexin 40, 43, or 45, the expression of which results in enhanced electrical coupling between cells. In another embodiment, genetically modified cells, recombinant virus or isolated nucleic acid encode a mutant, e.g., dominant negative, potassium (K) channel, e.g., a mutant Kir2.1, the expression of which in cells provides for enhanced depolarization. In another embodiment, genetically modified cells, recombinant virus or isolated nucleic acid encode a gene product, e.g., the gene product encoded by HCN genes, the expression of which in cells results in cells that have Purkinje-fiber characteristics, e.g., diastolic depolarization or $I_f$. In one embodiment, the reservoir of agent eluting device 224 includes a porous polymer to contain biologic agent 225. In one embodiment, biologic agent delivery device 220 is a transvascular device configured for distal end 221 to reach the endocardium of heart 199. In another embodiment, biologic agent delivery device 220 is a device configured for distal end 221 to reach the epicardium of heart 199. In one embodiment, biologic agent delivery device 220 represents a transvascular device such as a pacing lead, a guide wire, or a percutaneous transvascular catheter with an agent eluting device incorporated into its distal end. In one embodiment, biologic agent delivery device 220 includes a guide wire allowing for delivery of the biological agent. During a lead implantation procedure, the guide wire is transvenously inserted into heart 199 and removed after the lead is in place. In a specific embodiment, an over-the-wire lead is delivered over the guide wire. The biologic agent is delivered using the guide wire, which is removed after the lead is in place and the stimulation threshold is determined. Examples of such over-the-wire lead include the Guidant EASYTRAK® leads (Guidant Corporation, Saint Paul Minn.).

Figure 3:
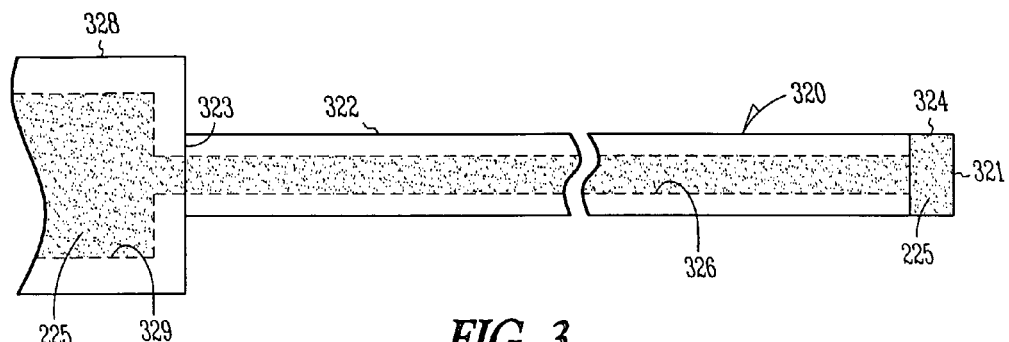
FIG. 3 is an illustration of an embodiment of a biologic agent delivery system.

FIG. 3 is an illustration of an embodiment of a biologic agent delivery system including a biologic agent delivery device 320 and an injection device 328. Biologic agent delivery device 320 includes a distal end 321, a proximal end 323, and an elongate body 322 coupled between distal end 321 and proximal end 323. Distal end 321 is configured to reach a stimulation site such as pacing site 117 or 118. Biologic agent delivery device 320 includes an agent eluting device 324 located at distal end 321. Agent eluting device 324 includes a reservoir that contains biologic agent 225. A lumen 326 extends within elongate body 322 from proximal end 323 to distal end 321. Lumen 326 includes a proximal opening at proximal end 323 and a distal opening coupled to agent eluting device 324. Injection device 328 includes a chamber 329, which is a reservoir that also contains biologic agent 225. Injection device 328 is configured to connect to biologic agent delivery device 320 to allow passage of biologic agent 225 from chamber 329 to agent eluting device 324 through lumen 326 to refill the reservoir of agent eluting device 324 when needed. In one embodiment, biologic agent delivery device 320 is a pacing lead with agent eluting device 324 incorporated onto its distal end, and injection device 328 represents a reservoir included in an implantable medical device which also delivers pacing pulses through the pacing lead.

Figure 4:
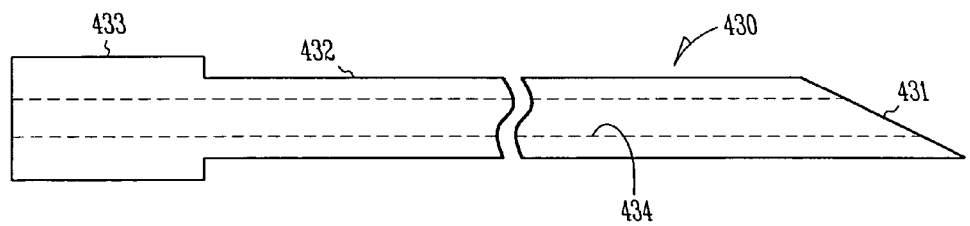
FIG. 4 is an illustration of an embodiment of another biologic agent delivery device.

FIG. 4 is an illustration of an embodiment of another biologic agent delivery device 430. Biologic agent delivery device 430 is a hollow needle including a needle tip 431, a rear end 433, a needle body 432 coupled between needle tip 431 and rear end 433, and a lumen 434 extending within needle body 432 from rear end 433 to needle tip 431. To deliver the biologic therapy, needle tip 431 penetrates tissue at the stimulation site, and biologic agent 225 is injected into the tissue through lumen 434.

Figure 5:
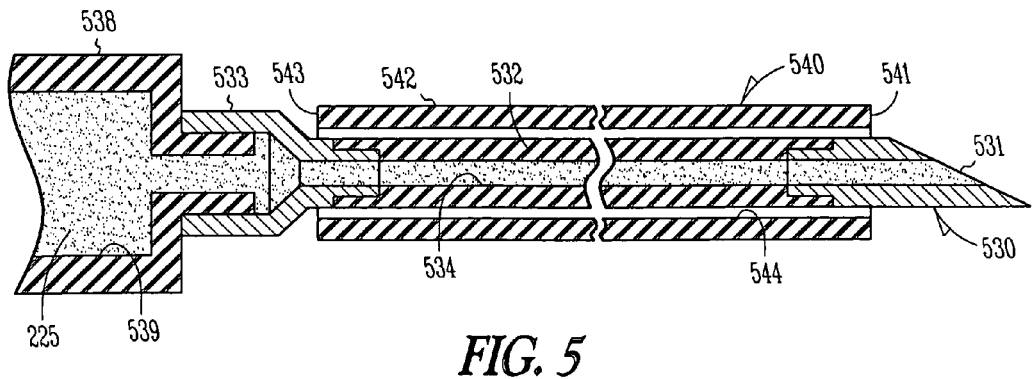
FIG. 5 is an illustration of an embodiment of another biologic agent delivery system.

FIG. 5 is an illustration of an embodiment of another biologic agent delivery system including a biologic agent delivery device 530, an injection device 538, and a transvascular device 540. Biologic agent delivery device 530 is a hollow needle including a needle tip 531, a rear end 533, a needle body 532 coupled between needle tip 531 and rear end 533, and a lumen 534 extending within needle body 532 from rear end 533 to needle tip 531. Needle body 532 is made of a flexible material. Transvascular device 540 includes a distal end 541, a proximal end 543, an elongate body 542, and a lumen 544 extending within elongate body 542. Lumen 544 includes a proximal opening at proximal end 543 and a distal opening at distal end 541 and is configured to accommodate at least a portion of biologic agent delivery device 530. Examples of transvascular device 540 include a pacing lead, a defibrillation lead, and a percutaneous transvascular catheter.

Injection device 538 includes a chamber 539, which is a reservoir that contains biologic agent 225. Injection device 538 is configured to connect to rear end 533 of biologic agent delivery device 530. To deliver the biologic therapy, transvascular device 540 is inserted into a blood vessel connected to the heart and advanced transvascularly until distal end 541 reaches a stimulation site. Biologic agent delivery device 530 is then inserted into lumen 544 such that needle tip 531 passes through lumen 544 and at least partially exits from the distal opening of lumen 544. Needle tip 531 penetrates tissue at the stimulation site to allow biologic agent 225 to be injected into the tissue through lumen 534.

Figure 7:
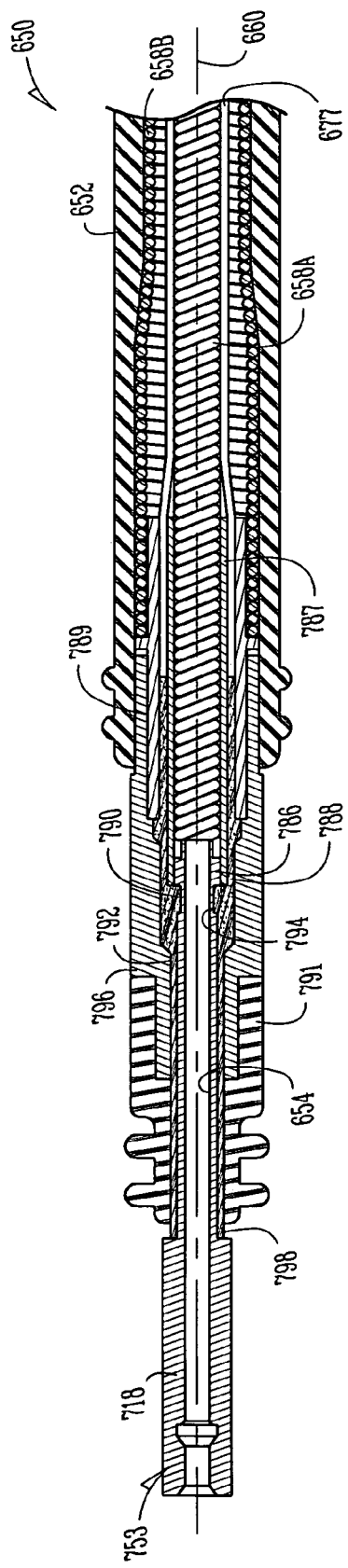
FIG. 7 is an illustration of an embodiment of a proximal end of the pacing lead including the biologic agent delivery device.

FIGS. 6A, 6B, and 7 illustrate a retractable bipolar pacing lead 650. In one embodiment, lead 650 represents a specific embodiment of a biologic agent delivery device (such as device 220 or 320) incorporated into a transvascular device. In another embodiment, lead 650 represents a specific embodiment of a transvascular device (such as device 540) including a lumen that accommodates at least a portion of a biologic agent delivery device (such as device 530). In another embodiment, lead 650 includes a biologic agent delivery device (such as device 220 or 320) and also includes a lumen that accommodates at least a portion of another, separate biologic agent delivery device (such as device 530).

FIGS. 6A and 6B are illustrations of an embodiment of a distal end 651 of retractable bipolar pacing lead 650. FIG. 6A illustrates lead distal end 651 when lead 650 is in a retracted position. FIG. 6B illustrates lead distal end 651 when lead 650 is in an extended position. As illustrated in FIGS. 6A and 6B, lead 650 includes a tip electrode and a ring electrode. The tip electrode includes a fixation helix 656, an electrode base 672, and an electrode collar 678 connecting fixation helix 656 and electrode base 672. Electrode base 672 and electrode collar 678 each have a tubular structure forming a portion of a lumen 654. Fixation helix 656 allows lead distal end 651 to be affixed to the intracardiac region. Electrode base 672 is mechanically connected to a conductor 658A, such that when conductor 658A rotates, the electrode base 672 translates along an axis 660 of lead 650. In a further embodiment, electrode base 672 is formed of an electrically conductive material, such as metal, and is electrically connected to conductor 658A. Disposed about electrode base 672 are external threads 676, which allow electrode base 672 to rotate and translate fixation helix 656. Electrode base 672 is coupled with an outer threaded shell 674. The ring electrode includes electrode 675, which is electrically connected to a conductor 658B. An inner insulation 677 electrically insulates conductors 658A and 658B from each other. A lead body 652 provides for an outer insulation for the conductors.

In one embodiment, components of the tip and ring electrodes are all made of conductive materials such as metals. Examples of material of which fixation helix 656 is made include stainless steel, platinum-iridium, and titanium. Examples of material of which electrode base 672 is made include stainless steel alloys. Examples of material of which electrode collar 678 is made include stainless steel and platinum-iridium alloys. Example of material of which electrode 675 is made includes platinum-iridium alloys.

Lead 650 includes an agent eluting collar 655 for delivering biologic agent 225. Agent eluting collar 655 is a specific embodiment of agent eluting device 224 or 324 and includes a reservoir containing biologic agent 225. In one embodiment, the reservoir includes a porous polymer containing biologic agent 225. In one embodiment, agent eluting collar 655 includes a reservoir containing biologic agent 225 and a means for controlled delivery of biologic agent 225. In another embodiment, agent eluting collar 655 includes the means for controlled delivery of biologic agent 225, and lead 650 includes a passageway providing for fluid communication between agent eluting collar 655 and the implantable medical device to which lead 655 is connected.

Lead body 652 forms the outer shell for a major portion of lead 650. Examples of material of which the outer shell is made include silicone and polyurethane.

In one embodiment, conductors 658A and 658B each include a coiled multifilar wire. Examples of material of which the coiled multifilar wire is made include stainless steel, stainless steel alloy MP35N, titanium, and tantalum.

In one embodiment, a steroid collar 662 is disposed within lead distal end 651 of the lead 650. Steroid collar 662 includes a steroidal substance that releases into the intracardiac region after lead distal end 651 is placed in that region. The steroidal substance reduces inflammation that is a response to the invasion of lead 650 into the intracardiac region.

Outer threaded shell 674 includes internal threads 682. As the electrode base 672 rotates, external threads 676 engage with internal threads 682 and translate electrode base 672 along axis 660. In one embodiment, lead 650 includes a stop to prevent fixation helix 656 from over-extension. In one embodiment, a stop 670 on internal threads 682 blocks the rotation of external threads 676. Once external threads 676 reach stop 670, electrode base 672 can no longer be rotated and translated. This prevents fixation helix 656 from being over-extended into the tissue of the intracardiac region. In one embodiment, a stop 666 is formed on an outer shell 680 to block the movement of electrode collar 678.

In one embodiment, outer threaded shell 674 and/or outer shell 680 are each formed of polyetheretherketone (PEEK). In one embodiment, outer threaded shell 674 is formed of PEEK 150 G, which has a low melt viscosity. For PEEK 150 G, the melt viscosity ranges from about 0.12-0.18 KNs/m$^2$, and the tensile strength is greater than or equal to 90 MPa. In another embodiment, outer threaded shell 674 is formed of PEEK 450 G, which has a standard melt viscosity. For PEEK 450 G, the melt viscosity ranges from about 0.38-0.50 KNs/m$^2$, and the tensile strength is greater than or equal to 90 MPa. PEEK allows outer threaded shell 674 to be molded, extruded, or machined for tighter tolerances or providing precision structures. PEEK is a tough rigid thermoplastic material that is biocompatible.

Proximal to lead distal end 651 of lead 650 is a fluoroscopy ring 664, as a radiopaque marker disposed about fixation helix 656. In one embodiment, as fixation helix 656 is extended out from lead 650, electrode collar 678 translates toward fluoroscopy ring 664 until abutting a portion fluoroscopy ring 664, at which point the fixation helix 656 is fully extended. Electrode collar 678 and fluoroscopy ring 664 allow viewing, under fluoroscopy, of whether fixation helix 656 is fully extended.

In one embodiment, outer shell 680 provides a stop for the translation of electrode collar 678. Outer shell 680 is coupled with outer threaded shell 674. In one embodiment, epoxy 668 is disposed between outer threaded shell 674 and outer shell 680. In one embodiment, epoxy 668 includes a blend of two different epoxies. The two different epoxies include EPOTEK® 353ND and EPOTEK® 353ND-T made by Epoxy Technology. They are mixed in the ratio of 1 part EPOTEK® 353ND to 1.75 parts EPOTEK® 353ND-T. Epoxy 668 is cured at a temperature of 150° C. for one hour.

FIG. 7 is a detailed illustration of one embodiment of a lead proximal end 753 of lead 650 (as a specific embodiment of lead 100B). Lead proximal end 753 includes a terminal pin 718, which is mechanically and electrically coupled to conductor 658A. Terminal pin 718 provides the electrical connection between implantable device 370 and the tip electrode of lead 650 though conductor 658A. A connective crimp tube 787 reinforces the connection between terminal pin 718 and conductor 658A. As terminal pin 718 is rotated, conductor 658A rotates, thereby rotating electrode base 672, electrode collar 678, and fixation helix 656. Terminal pin 718 has a tubular structure that forms a proximal portion of lumen 654.

Lead 650 further includes an outer terminal ring 796 that is electrically coupled to conductor 658B through a conductive collar 789 to provide the electrical connection between implantable device 370 and the ring electrode (675) of lead 650 though conductor 658B. An insulator sleeve 798 is disposed over at least a portion of terminal pin 718, to insulate terminal pin 718 from outer terminal ring 796. In one embodiment, sleeve 798 rotates with outer terminal ring 796. In one embodiment, sleeve 798 is coupled to terminal pin 718 with a snap-fit connection. In another embodiment, sleeve 798 is also coupled to outer terminal ring 796 with a snap-fit connection. In one embodiment, sleeve 798 includes a shoulder 790. Shoulder 790 is engaged with a recess 794 of terminal pin 718, and prevents terminal pin 718 from moving axially. In one embodiment, shoulder 790 includes an annular shoulder disposed about the circumference of sleeve 798, which allows terminal pin 718 to rotate relative to outer terminal ring 796. The annular shoulder engages within an annular recess disposed within the circumference of terminal pin 718. In another embodiment, sleeve 798 further includes at least one recess 788 disposed adjacent to shoulder 790. Recess 788 receives a shoulder 786 of terminal pin 718. In another embodiment, sleeve 798 further includes a stop 792 for outer terminal ring 796. Terminal pin body 791 provides increased axial strength to the connection between lead 650 and implantable device 370.

Terminal pin 718 and outer terminal ring 796 are each made of conductive materials such as metals. Examples of material of which terminal pin 718 is made include stainless steel, titanium, and platinum-iridium. Examples of material of which terminal ring 796 is made include stainless steel, titanium, and platinum-iridium.

Sleeve 798 is formed of non-conductive material. In one embodiment, sleeve 798 is formed of PEEK. In one embodiment, sleeve 798 is formed of PEEK 150 G. In another embodiment, sleeve 798 is formed of PEEK 450 G. The PEEK allows sleeve 798 to be molded, extruded, or machined for tighter tolerances or providing precision structures.

Lumen 654 extends along axis 660 throughout lead 650, and has a substantially circular cross-section perpendicular to axis 660. As illustrated in FIGS. 6A, 6B, and 7, lumen 654 is formed directly by the tip electrode of lead 650, conductor 656, and terminal pin 718. Lumen 654 has a distal opening at lead distal end 651 and a proximal opening at lead proximal end 616. In one embodiment, the substantially circular cross-section has a substantially uniform diameter throughout lead 650. This diameter is of a size accommodating at least a portion of biologic agent delivery device 530 and allowing needle tip 531 to pass through lumen 654 and at least partially exits from lead distal end 651.

Generally, metals used for components of lead 650, as illustrated in FIGS. 6A, 6B, and 7, include stainless steel, titanium, niobium, platinum-iridium alloys, other alloys such as elgiloy and nickel/titanium alloys. Non-metal materials used for components of lead 650, as illustrated in FIGS. 6A, 6B, and 7, include silicone, polyurethane, polydimethyls, siloxanes, and PEEK.

Other embodiments of the detailed structure and elements of lead 650 are available by adopting and/or modifying existing lead structures and elements to include lumen 654. Examples of such existing lead structures and elements are discussed in U.S. Pat. No. 6,141,594, "SINGLE PASS LEAD AND SYSTEM WITH ACTIVE AND PASSIVE FIXATION ELEMENTS," U.S. Pat. No. 6,463,334, "EXTENDABLE END RETRACTABLE LEAD," U.S. Pat. No. 6,915,169, "EXTENDABLE AND RETRACTABLE LEAD HAVING A SNAP-FIT TERMINAL CONNECTOR," both assigned to Cardiac Pacemakers, Inc., which are incorporated herein by reference in their entirety.

Figure 8:
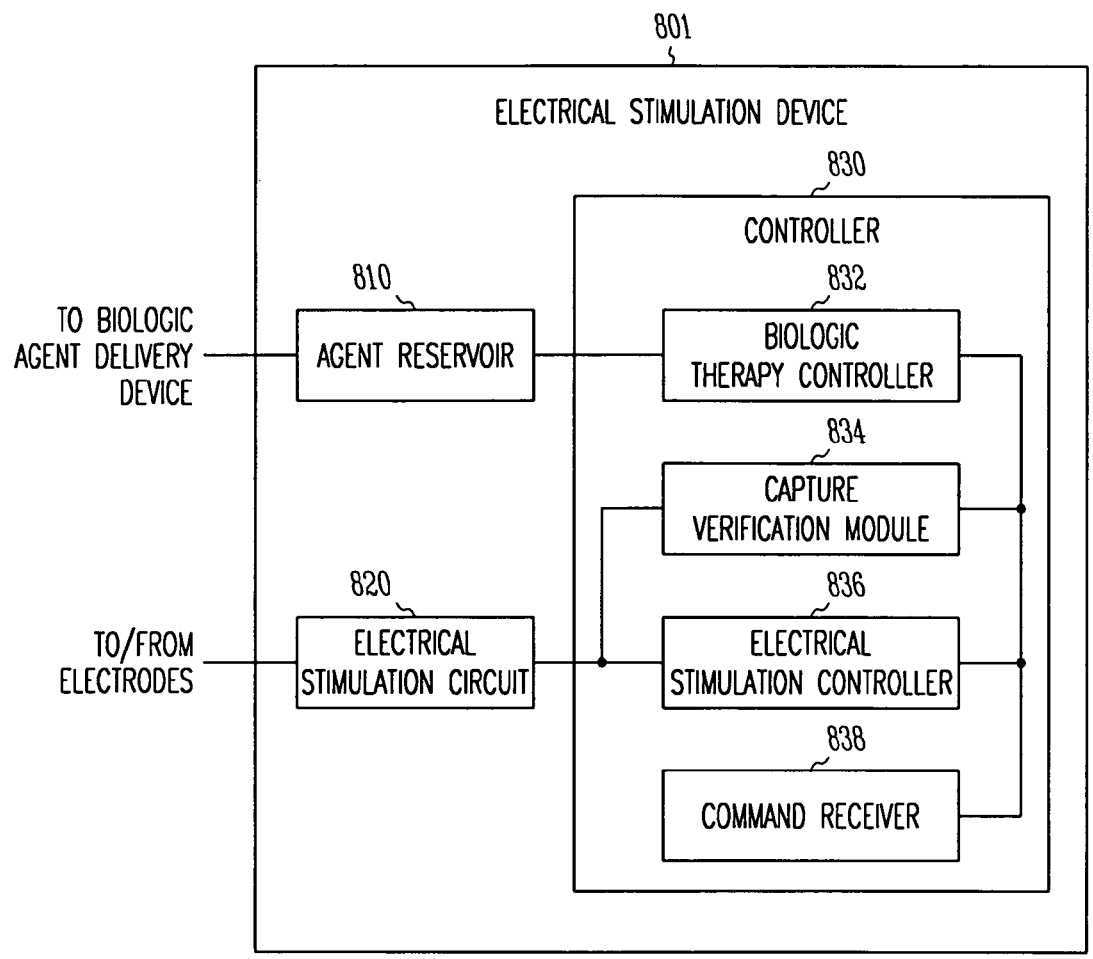
FIG. 8 is a block diagram illustrating an embodiment of an electrical stimulation device.

FIG. 8 is a block diagram illustrating an embodiment of an electrical stimulation device 801. In one embodiment, electrical stimulation device 801 is an implantable electrical stimulation device being a specific embodiment of implantable medical device 101. In another embodiment, electrical stimulation device 801 is an external (non-implantable) electrical stimulation device. In the embodiment as illustrated in FIG. 8, electrical stimulation device 801 includes an agent reservoir 810, an electrical stimulation circuit 820, and a controller 830 that controls the delivery of both a biologic therapy and an electrical therapy. The biologic therapy is delivered to modify tissue so as to lower the stimulation threshold for each stimulation site to which the electrical therapy is delivered. This embodiment allows repeated delivery of the biologic therapy while the electrical therapy is delivered. In another embodiment, electrical stimulation device 801 delivers only the electrical therapy. The biologic therapy is delivered using a separate biologic agent delivery device. In one embodiment, a biologic agent delivered to the stimulation site modifies the tissue property of the stimulation site permanently, such that the biologic therapy needs to be delivered only once, before or at the beginning of the electrical therapy.

Agent reservoir 810 stores biologic agent 225. To deliver biologic agent 225, agent reservoir 810 is connected to a biologic agent delivery device such as device 320, including lead 650 as a specific embodiment. Agent reservoir 810 is configured to connect to the proximal opening of lumen 326 of device 320 to allow passage of biologic agent 225 through lumen 326. With lead 650, agent reservoir 810 is configured to connect to the passageway of lead 650, which provides for fluid communication between agent eluting collar 655 and agent reservoir 810.

Electrical stimulation circuit 820 delivers electrical stimulation pulses to stimulation sites through electrodes. Examples of the electrical stimulation pulses include cardiac pacing pulses, cardioversion/defibrillation pulses, neural stimulation pulses, and other electrical pulses delivered to cause tissue excitation. After the biologic therapy, each electrode placed in a stimulation site is substantially surrounded by tissue that has been genetically modified to lower the stimulation threshold.

Controller 830 includes a biologic therapy controller 832, a capture verification module 834, an electrical stimulation controller 836, and a command receiver 838. Biologic therapy controller 832 controls the delivery of biologic agent 225. In one embodiment, in which the biologic therapy is to be repeatedly delivered, biologic therapy controller 832 controls the delivery of biologic agent 225 according to a predetermined schedule, such as on a periodic basis. In another embodiment, biologic therapy controller 832 controls the delivery of biologic agent 225 in response to a command. In a specific embodiment, in which electrical stimulation device is an implantable electrical stimulation device, the command is entered through an external system communicatively coupled to the electrical stimulation device via telemetry and received by command receiver 838. In another embodiment, capture verification module 834 detects a non-capture by detecting an evoked potential in response to each electrical stimulation pulse delivered to each stimulation site. The non-capture is detected when the evoked potential is not detected. After a predetermined number of non-captures are detected, capture verification module 834 produces the command. The command receiver 838 receives that command. In one embodiment, biologic therapy controller 832 controls the delivery of biologic agent 225 when command receiver 838 receives the command from the external system and/or capture verification module 834. Electrical stimulation controller 836 controls the delivery of the electrical stimulation pulses from electrical stimulation circuit 820.

In one embodiment, electrical stimulation device 801 includes an implantable cardiac pacemaker that delivers pacing pulses to one or more pacing sites of a heart. In general, the delivery of biologic agent 225 to each pacing site lowers the pacing threshold and hence, the programmed pacing energy delivered to that site. In a specific embodiment, the implantable cardiac pacemaker delivers a CRT by delivering pacing pulses to a plurality of predetermined pacing sites to substantially improve the synchronization of ventricular contraction of the heart. Delivery of biologic agent 225 to these predetermined pacing sites eliminates or reduces the need for moving one or more of these pacing sites for the reason of a particularly high pacing threshold. In another specific embodiment, the implantable cardiac pacemaker delivers a post myocardial infarction pacing therapy by delivering pacing pulses to one or more pacing sites each including infarct tissue that tends to have a particularly high pacing threshold.

Figure 9:
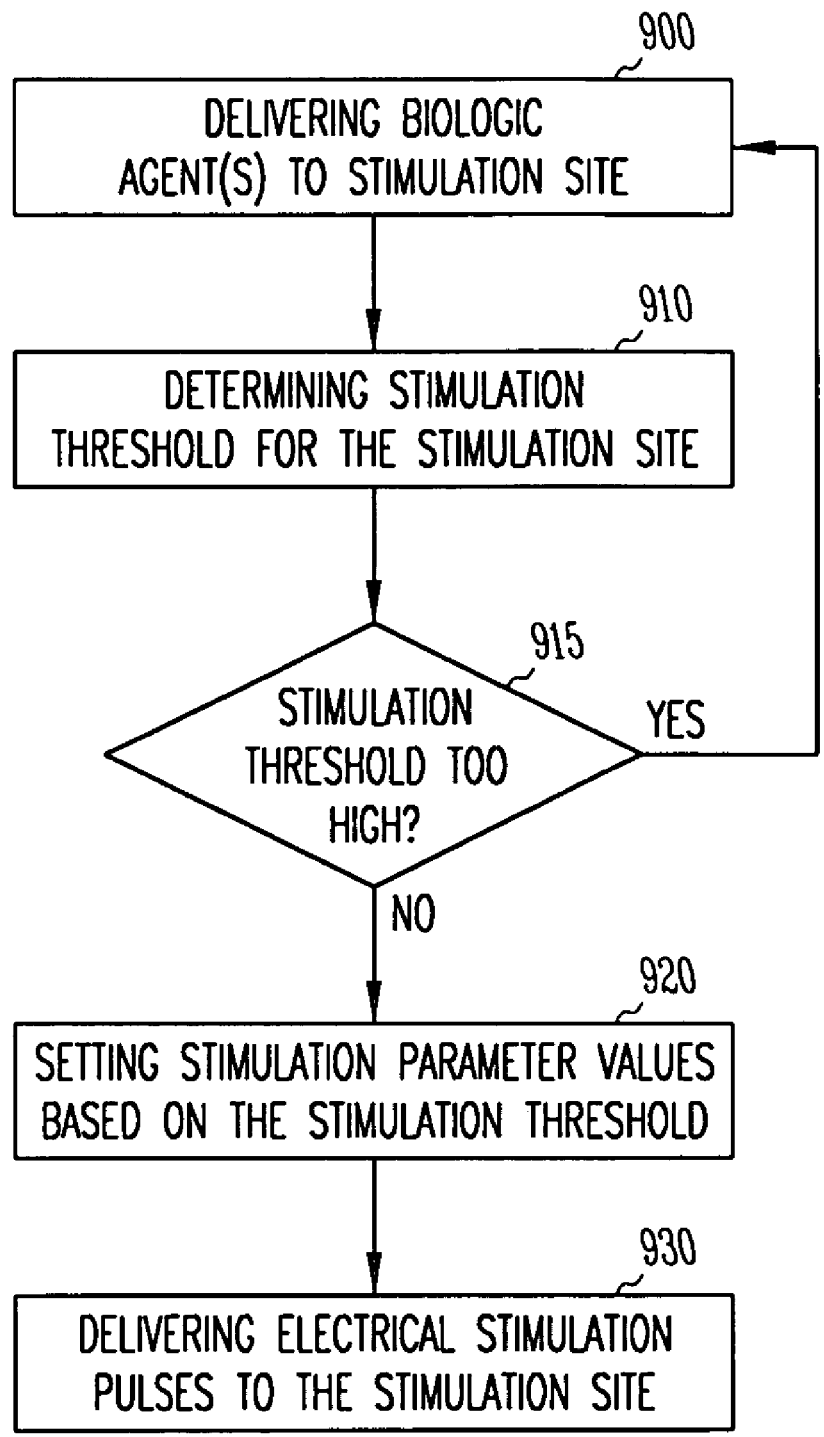
FIG. 9 is a flow chart illustrating an embodiment of a method for delivering electrical stimulation pulses to a stimulation site.

FIG. 9 is a flow chart illustrating an embodiment of a method for delivering electrical stimulation pulses to a stimulation site. The method includes modifying tissue at the stimulation site to lower the stimulation threshold, which represents the minimum energy required to electrically excite the tissue at the stimulation site. In a specific embodiment, the method is applied for delivering cardiac pacing pulses to a pacing site, and the stimulation threshold is a pacing threshold. In another specific embodiment, the method is applied for delivering neural stimulation pulses to a neural stimulation site, and the stimulation threshold is a neural stimulation threshold. In various embodiments, the method is applied for delivering electrical stimulation pulses to multiple stimulation sites, with steps 900-930 repeatedly performed for each stimulation site.

At least one biologic agent is delivered to a stimulation site at 900. The biologic agent modifies tissue property at the stimulation site to lower a stimulation threshold. Examples of the biologic agent include one or more of genetically modified cells, recombinant viruses, or isolated nucleic acid, which may include a transcriptional element (e.g., a promoter) regulatable by an electric field created by the pacing pulses, operably linked to an open reading frame for a gene product. In one embodiment, the biologic agent modifies sodium (Na) or L-type calcium (Ca) channels in the tissue to increase excitability of cells and/or causes overexpression of connexin 40, 43, or 45 which enhances electrical coupling between cells. In one embodiment, the biologic agent includes an open reading frame for a gene product that alters the amount or activity of potassium (K) channels, or yields cells with Purkinje-fiber characteristics. In one embodiment, for cell-based biological agents, the cells are conditioned in vitro prior to the delivery to the stimulation site to expedite the modification of tissue property.

In one embodiment, the biologic agent is released from an agent eluting device including a polymer containing the biologic agent. In another embodiment, the biologic agent is injected using a hollow needle including a needle tip transvascularly advanced to the stimulation site. In another embodiment, the biologic agent is released from an implantable medical device including an agent reservoir containing the at least one biologic agent. In another embodiment, the biological agent is delivered through a guide wire that is inserted and removed during a lead implantation procedure. For example, an over-the-wire lead is delivered over the guide wire. The biologic agent is delivered through the guide wire, which is removed after the lead is in place and the stimulation threshold is determined. Examples of such an over-the-wire lead include the Guidant EASYTRAK® leads. In various embodiments, the biologic agent is delivered using a biologic agent delivery device or system described above with reference to FIGS. 2-7.

In one embodiment, the biologic agent is delivered to the stimulation site once to genetically modify the tissue property at the stimulation site. In another embodiment, the biologic agent is delivered to the stimulation site repeatedly to maintain a lowered stimulation threshold. In a specific embodiment, the biologic agent is delivered to the stimulation site according to a predetermined schedule, such as on a periodic basis. In another specific embodiment, the biologic agent is delivered to the stimulation site agent in response to a command, such as a command automatically generated when one or more electrical stimulation pulses fail to excite tissue at the stimulation site, or a command entered by a physician or other caregiver.

The stimulation threshold for the stimulation site is determined at 910, after the biologic agent delivered to the stimulation site has sufficient time to modify the tissue property. The stimulation threshold is determined by delivering stimulation pulses at different energy levels to the stimulation site and detect whether each stimulation pulse evokes a response indicative of tissue excitation. The lowest energy level at which a stimulation pulse evokes the response indicative of tissue excitation is taken as the stimulation threshold. In various embodiments, the energy level of a stimulation pulse is determined by parameters including a stimulation amplitude and a stimulation pulse width. The different energy levels used in the determination of the stimulation threshold are controlled by different combinations of stimulation amplitude and stimulation pulse width. The determined stimulation threshold is the combination of a stimulation amplitude and a stimulation pulse width.

If the stimulation threshold determined at 910 is considered too high at 915, the delivery of the biologic agent at 900 is repeated. If the stimulation threshold determined at 910 is considered adequate, values for stimulation parameters are set based on the stimulation threshold at 920. The values of the stimulation parameters are set for each stimulation pulse to have an energy level exceeding the stimulation threshold by a safety margin. In one embodiment, the safety margin is a predetermined amount of energy. In another embodiment, the safety margin is a predetermined percentage of the stimulation threshold.

Electrical stimulation pulses are delivered to the stimulation site using the stimulation parameters at 930. The delivery of the biologic agent at 900 eliminates the need to change one or more stimulation sites to avoid a particularly high stimulation threshold, thereby improving the efficacy and/or efficiency of an electrical stimulation therapy.

While cardiac pacing is specifically discussed in this document as a specific example, the present subject matter generally applies to all electrical stimulation and other therapies that elicit a tissue response. For example, genetically modifying nervous tissue by delivering a biologic agent to a particular nerve in a nerve bundle renders this particular nerve more sensitive to a stimulus, such as an electric filed or electrical pulse applied to the nerve bundle. This permits selective neural stimulation of the genetically modified nerve without activating the adjoining nerves. The excitation characteristics of smooth muscle, for example in the stomach or intestines, may be modified to permit electrical stimulation of these tissues at lower energy. The present subject matter can also be applied to genetically modify tissue characteristics to make a portion of tissue more sensitive to an applied physical, pharmacological, or any other types of therapy.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering electrical stimulation pulses to at least one stimulation site in a body, the system comprising:

at least one biologic agent encoding a gene product for modifying tissue to lower a stimulation threshold, the at least one biologic agent including a transcriptional element regulatable by an electric field created by the electrical stimulation pulses delivered to the at least one stimulation site in the body, the transcriptional element operably linked to an open reading frame for the gene product;

a reservoir containing the at least one biologic agent;

a biologic agent delivery device including the reservoir or coupled to the reservoir, the biologic agent delivery device including at least a portion configured to reach the at least one stimulation site to deliver the at least one biologic agent from the reservoir to the at least one stimulation site; and a biological therapy controller coupled to the biological agent delivery device and adapted to detect evoked potentials in response to the electrical stimulation pulses delivered to the at least one stimulation site and control the delivery of the at least one biologic agent based on whether the evoked potentials are detected.

2. The system of claim 1, wherein the at least one biologic agent comprises genetically modified stem cells.

3. The system of claim 1, wherein the at least one biologic agent comprises recombinant virus.

4. The system of claim 1, wherein the at least one biologic agent comprises isolated nucleic acid.

5. The system of claim 1, wherein the gene product modifies the amount or activity of sodium (Na) channels.

6. The system of claim 1, wherein the gene product modifies the amount or activity of calcium (Ca) channels.

7. The system of claim 1, wherein the gene product increases the amount or activity of connexin 40, 43, or 45.

8. The system of claim 1, wherein the gene product modifies the amount or activity of potassium (K) channels.

9. The system of claim 1, wherein the gene product modifies diastolic depolarization.

10. The system of claim 1, wherein the biologic agent delivery device comprises a proximal end, a distal end, and an elongate body coupled between the proximal end and the distal end, the distal end configured to reach the at least one stimulation site.

11. The system of claim 10, wherein the biologic agent delivery device comprises a transvascular biologic agent delivery device including an agent eluting device at the distal end, the agent eluting device including the reservoir.

12. The system of claim 11, wherein the reservoir comprises a porous polymer.

13. The system of claim 11, wherein the biologic agent delivery device comprises a lumen extending within the elongate body, the lumen including a proximal opening at the proximal end and a distal opening at the distal end, and further comprising an injection device including the reservoir having a chamber containing the at least one biologic agent, the injection device configured to connect to the proximal opening of the lumen to allow passage of the at least one biologic agent from the chamber to the lumen.

14. The system of claim 1, wherein the biologic agent delivery device comprises a hollow needle including a needle tip, a rear end, and a needle body coupled between the needle tip and the rear end, the hollow needle configured to allow the needle tip to reach the at least one stimulation site, and further comprising an injection device including the reservoir, the injection device configured to connect to the rear end of the hollow needle to allow injection of the at least one agent through the hollow needle.

15. The system of claim 14, wherein the needle body is flexible, and further comprising a transvascular device including a proximal end, a distal end, an elongate body coupled between the proximal end and the distal end, and a lumen extending within the elongate body, the lumen including a proximal opening at the proximal end and a distal opening at the distal end and configured to accommodate at least a portion of the hollow needle and to allow the needle tip to pass through the lumen and to at least partially exit from the distal opening and enter the at least one stimulation site.

16. The system of claim 1, further comprising an electrical stimulation device adapted to deliver the electrical stimulation pulses to the at least one stimulation site.

17. The system of claim 16, wherein the electrical stimulation device comprises an implantable electrical stimulation device including the biologic therapy controller.

18. The system of claim 16, wherein the electrical stimulation device comprises an implantable pacemaker.

19. The system of claim 18, wherein the implantable pacemaker is adapted to deliver a cardiac resynchronization therapy by delivering the pacing pulses to a plurality of cardiac locations including the at least one stimulation site.

20. The system of claim 18, wherein the implantable pacemaker is adapted to deliver a post myocardial infarction pacing therapy by delivering the pacing pulses to one or more infarct regions including the at least one stimulation site.

21. The system of claim 16, wherein the electrical stimulation device comprises a neural stimulator.

22. The system of claim 16, wherein the biologic agent delivery device comprises a proximal end, a distal end, an elongate body coupled between the proximal end and the distal end, and a lumen extending within the elongate body, the distal end configured to reach the at least one stimulation site, the lumen including a proximal opening at the proximal end and a distal opening at the distal end, and wherein the electrical stimulation device comprises an implantable electrical stimulation device including the reservoir, wherein the reservoir is configured to connect to the proximal opening of the lumen to allow passage of the at least one agent from the reservoir to the lumen.

23. A method for delivering electrical stimulation pulses to at least one stimulation site in a body, the method comprising:

delivering at least one biologic agent to the at least one stimulation site using a biologic agent delivery device configured to reach the at least one stimulation site, the at least one biologic agent encoding a gene product for modifying tissue in the at least one stimulation site to lower a stimulation threshold, the gene product including a transcriptional element regulatable by an electric field created by the electrical stimulation pulses delivered to the at least one stimulation site in the body, the transcriptional element operably linked to an open reading frame for the gene product;

delivering the electrical stimulation pulses to the at least one stimulation site;

detecting evoked potentials each in response to one of the electrical stimulation pulses delivered to the at least one stimulation site; and controlling the delivering the at least one biologic agent to the at least one stimulation site using an outcome of the detecting the evoked potentials.

24. The method of claim 23, further comprising conditioning the at least one biologic agent in vitro.

25. The method of claim 23, wherein the at least one biologic agent comprises genetically modified stem cells.

26. The method of claim 23, wherein the at least one biologic agent comprises recombinant virus.

27. The method of claim 23, wherein the at least one biologic agent comprises isolated nucleic acid.

28. The method of claim 23, wherein the at least one biologic agent encodes a gene product that modifies the amount or activity of sodium (Na) channels.

29. The method of claim 23, wherein the at least one biologic agent encodes a gene product that modifies the amount or activity of calcium (Ca) channels.

30. The method of claim 23, wherein the at least one biologic agent encodes connexin 40, 43, or 45.

31. The method of claim 23, wherein the at least one biologic agent encodes a gene product that modifies the amount or activity of potassium (K) channels.

32. The method of claim 23, wherein the at least one biologic agent encodes a gene product that modifies the amount or activity of diastolic depolarization.

33. The method of claim 23, wherein delivering the at least one biologic agent comprises releasing the at least one biologic agent from an agent eluting device including a polymer containing the at least one biologic agent.

34. The method of claim 23, wherein delivering the at least one biologic agent comprises injecting the at least one biologic agent using a hollow needle including a needle tip transvascularly advanced to the stimulation site.

35. The method of claim 23, wherein delivering the at least one biologic agent comprises releasing the at least one biologic agent from an implantable medical device including an agent reservoir containing the at least one biologic agent.

36. The method of claim 35, wherein releasing the at least one biologic agent from an implantable medical device comprises releasing the at least one biologic agent according to a predetermined schedule.

37. The method of claim 35, wherein releasing the at least one biologic agent from an implantable medical device comprises releasing the at least one biologic agent in response to a command received from an external system communicatively coupled to the implantable medical device.

38. The method of claim 23, wherein delivering the at least one biologic agent to the at least one stimulation site comprises delivering the at least one biologic agent to a neural stimulation site including portions of selected one or more nerves of a nerve bundle to lower the stimulation threshold of the selected one or more nerves to allow selective stimulation of the selected one or more nerves by the electrical stimulation pulses without activating adjoining nerves of the nerve bundle.

* * * * *

UNITED STATES PATENT AND TRADEMARK OFFICE
CERTIFICATE OF CORRECTION

PATENT NO. : 7,630,761 B2  Page 1 of 1
APPLICATION NO. : 11/267654
DATED : December 8, 2009
INVENTOR(S) : Salo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 974 days.

Signed and Sealed this

Twenty-first Day of December, 2010

David J. Kappos
*Director of the United States Patent and Trademark Office*